United States Patent [19]

Bower et al.

[11] Patent Number: 4,574,615

[45] Date of Patent: Mar. 11, 1986

[54] SONIC APPARATUS AND METHOD FOR DETECTING THE PRESENCE OF A GASEOUS SUBSTANCE IN A CLOSED SPACE

[75] Inventors: John R. Bower, Lynchburg, Va.; Charles W. Hammond, Lancaster, Ohio

[73] Assignee: The Babcock & Wilcox Company, New Orleans, La.

[21] Appl. No.: 562,558

[22] Filed: Dec. 19, 1983

[51] Int. Cl.[4] ............................................. G01N 31/00
[52] U.S. Cl. ........................................ 73/24; 73/592; 73/597; 73/703
[58] Field of Search .......... 55/15; 73/703, 24, 40.5 A, 73/591, 592, 597; 367/117; 24/500, 499, 509

[56] References Cited

U.S. PATENT DOCUMENTS

| 4,386,527 | 6/1983 | Maucher | 73/597 |
| 4,432,231 | 2/1984 | Napp et al. | 73/644 |

FOREIGN PATENT DOCUMENTS

| 424105 | 1/1926 | Fed. Rep. of Germany | 24/509 |
| 569630 | 11/1957 | Italy | 24/509 |
| 2087559 | 5/1982 | United Kingdom | 73/24 |
| 699416 | 11/1979 | U.S.S.R. | 73/24 |

OTHER PUBLICATIONS

Meredith R. W., Digital Data Acquisition System for Measuring Free Decay of Acoustical Standing Waves in a Resonant Tube, Rev. Sci. Instrum. 55(1) 1/84, pp. 116-118, (73-24).

*Primary Examiner*—Bernard Nozick
*Attorney, Agent, or Firm*—Robert J. Edwards; James C. Simmons; D. Neil LaHaye

[57] ABSTRACT

A method and apparatus for detecting the presence of a gaseous substance within a space bounded by an enclosure utilizes the fact that sound is not transmitted through a vacuum and is transmitted through the material of the enclosure. A sonic wave transmitter and a sonic wave receiver are engaged with the material of the enclosure and separated by the space. Using the calculated arrival times and/or amplitudes for the soundwave portions through the space and through the material of the enclosure, it can be determined whether a soundwave portion has passed through the space and thus a leakage of gaseous substance into the space above a threshold amount has taken place.

19 Claims, 4 Drawing Figures

SONIC APPARATUS AND METHOD FOR DETECTING THE PRESENCE OF A GASEOUS SUBSTANCE IN A CLOSED SPACE

The present invention relates in general to detecting equipment and in particular to a new and useful method and apparatus of detecting the presence of a gaseous substance in a closed space.

Thermally insulated tubular structures having at least one inner tube and an outer tube are known and used, for example, as insulated steam injection tubing in oil wells or in pipe lines for carrying fluids at elevated or low temperatures. Such piping is disclosed, for example, in U.S. Pat. No. 3,574,357 to Alexandru et al and U.S. Pat. No. 3,397,345 to Owens et al.

It is known to provide a vacuum in the annular space between the inner and outer tubes to act as a thermal barrier for insulation of the steam injection tubing. Since the effectiveness of the insulation is dependent on the maintenance of the vacuum, it is important to be able to obtain a signal indicative of the pressure condition within the annular space. This is difficult because of the inherent inaccessibility of the annular space within the tubing.

It is an object of the present invention to utilize non-destructive, non-intrusive, and simple apparatus for determining loss of vacuum in an enclosed space such as between the inner and outer tubes of insulated steam injection tubing in the field.

Another object of the invention is to provide such a device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

IN THE DRAWINGS

Figure 1:
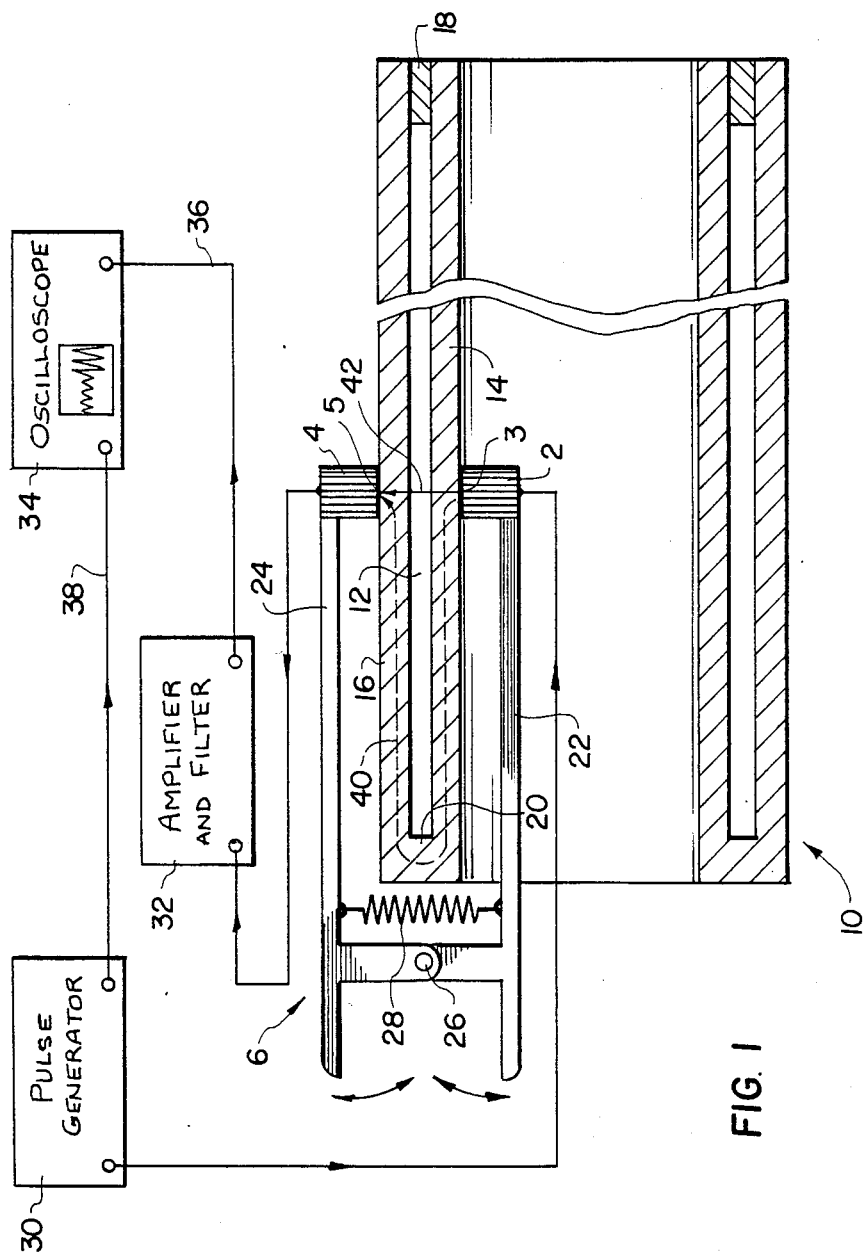
FIG. 1 is a schematic representation of a device embodying the present invention in position for testing the pressure condition in the annular space of an insulated steam injection tube, which is shown in cross section.

Referring to the drawings in particular, FIG. 1 illustrates a device for determining the pressure condition in the annular space 12 of an insulated steam injection tube 10. Space 12 is disposed between an inner tube 14 and an outer tube 16 and is bounded at one end by a sealing means such as, for example, an annular plug or sealing assembly 18. At the opposite end of tube 10, the annular space is bounded by another sealing means such as, for example, a continuous connection 20 between the inner and outer tubes which is made of the same or similar material as the tubes 14 and 16. Although it is not necessary to the present invention that the structure at either end of space 12 have any specific characteristic, it is preferred that at least one of the structures conduct sonic waves at a predictable speed.

The basic principle utilized by the present invention is that sound can travel through a space only if there is air or other gas present. The invention utilizes equipment for generating and/or processing sonic waves.

Figure 2:
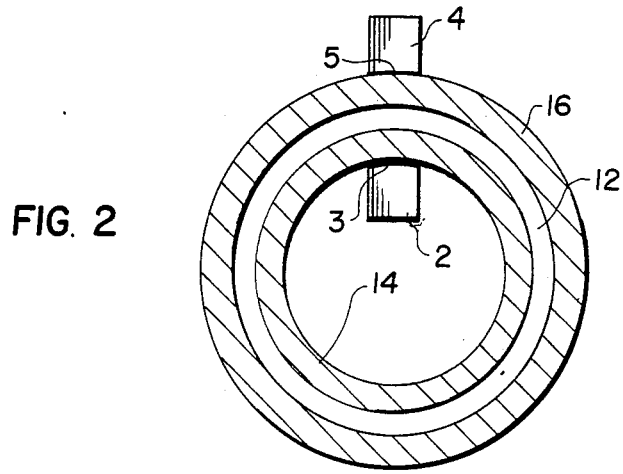
FIG. 2 is a transverse sectional view of the tubing showing the positions of the two transducers of the device.

The device itself comprises a first transducer 2 and a second transducer 4. The first and second transducers are mounted on mounting means which are generally designated 6 made of a pair of arms 22 and 24 which are hinged together at a hinge 26. Biasing means in the form of a spring 28 urge the transducers 2 and 4 together, the length of arms 22 and 24 being selected to position transducer 2 at a first point and transducer 4 at a second point on the inner and outer walls of the respective tubes forming the enclosure. As shown in FIG. 2, the surface of transducer 4 for contacting the outer surface of outer tube 16 at a second point 5 is curved concavely, and the surface of transducer 2 for contacting the inner surface of the inner tube 14 at a first point 3 is curved convexly. The first point 3 is selected to be separated from the second point 5 by space 12 with the first and second points being spaced from connection 20.

In operation of the device, the arms 22 and 24 are urged apart against the bias of spring 28 so that the transducers 2 and 4 can be clipped into engagement with the inner and outer surfaces of the insulated steam injection tube 10. To ensure even closer acoustic coupling between the transducers and the tubes, the surfaces of the transducers to be brought into contact with the tubes may be coated with a suitable oil or grease.

A pulse generator 30 for generating high voltage electrical pulses is connected to one of the transducers such as the first transducer 2 which converts the electrical pulses to ultrasonic pulses. The other or second transducer 4 is connected to an amplifier and filter circuit 32.

A detector in the form of an oscilloscope 34 is provided with a first input line 36 for providing a signal proportional to the sonic wave received by the detector transducer 4, and a second input line 38 from the pulse generator 30 for generating a trigger signal to begin scanning of the oscilloscope for each cycle of operation.

Since the material of the inner and outer tubes 14 and 16 respectively as well as the plug 18 and connecting material 20 is known, the speed of the ultrasonic wave through this material is also known. The speed can be correlated with the scanning speed of the oscillosocope 34 so that the position of an expected signal due to the sonic wave passing through the material of the tube 10 via the connecting material 20 along the path length illustrated at 40 can be noted. Whether gas is present in the annular space 12 or not, at least this sonic detection will thus be displayed on oscilloscope 34.

Since in general the tubes are made of metal, and it is known that sonic waves pass more quickly through metal than through gas which might be in the space 6, the locations of the transducers along the tube are preferably selected so that the path length 40 for the sonic wave through the material of the tube via connection 20 is much longer than the path length illustrated at 42 across the space 6. By thus selecting the path lengths 40 and 42 by determining, identifying, and taking into account the speeds of sound through the gas in the space and the material of the tube, it may be insured that a sonic wave portion passing along path length 42 through the space (because of gas in the space) will reach the detecting transducers 4 before a sonic wave portion passing along path length 40 through the material.

By knowing the length of time for a sonic wave to travel through the space along path length 42, the oscilloscope 34 can be used to establish if and to what extent a sonic wave has passed through the space 12. With the space normally under a vacuum of such a magnitude that sound cannot pass therethrough, if sound does pass through the space, it is indicative that some gas has leaked to the space and the pressure therein has increased at least to a threshold amount which allows passage of sound.

By experiment it is found that a pressure as low as 0.1 atmospheres can be detected using the apparatus, and it is expected that even lower pressures can be detected using the apparatus and techniques of this invention as experience therewith grows. Since sound travels on the order of 20 times faster in metal than in air (a typical gas that would be found in space 12 upon the occurrence of a leak), path length 40 is preferably selected to be 20 times greater than path length 42 plus an additional distance to allow a sufficient additional time for a few air path waves to be detected on the oscilloscope before metal path waves are detected. With a typical spacing gap of 0.4 inches for annular space 12, the path length 40 for sonic waves passing through the material is selected to preferably be about 1 foot or more.

In practicing a preferred method of the invention, transducer 2 provides at a first point 3 on the inner surface of inner tube 14 forming part of the enclosure short duration bursts of ultrasound. A first portion of this sound passes in all directions through the material of the tubular enclosure and, if a threshold amount of air or other gas is present in space 12, another portion of the sound passes through the path length 42 defined in the space. Although it is not known exactly what the threshold pressure is in a space for passage of sound therethrough, it is believed that the threshold pressure corresponds roughly to a pressure which would result in deterioration of insulating effects thereof. After the triggering pulse provided by line 38, the first pulse to be received at the second point 5 on the outer surface of outer tube 16 forming part of the enclosure is the pulse corresponding to the portion of sound passing through the space along path length 42 if there is a threshold pressure in the space. The amplitude of this signal varies with the amount of air or other gas in space 12. The second pulse to be received at the second point 5 is of a much greater amplitude (on the order of a thousand times greater) and is constant since it represents the sound passing along path length 40 through the material of the enclosure. Of course, if a threshold pressure for passage of sound through the space is not present, then only this second pulse will be detected. Although as a practical matter the second pulse will be detected, it is not essential to the present invention that it be detected. For example, if a sonic wave portion is detected at transducer 4 at the time at which it is calculated that a sonic wave portion passing through the space will arrive, or if one or more of the detected sonic wave portions has a compared amplitude which corresponds to the amplitude of a sonic wave portion which travels through a gaseous substance in the space, it is indicative of a portion of the sonic wave passing through the space.

Since electronic noise and some mechanical noise is always present and may be a particular problem in an oil field when dealing with full size insulated steam injection tubing, a single test may not establish a conclusive result. At the time the first and, more importantly, the second portion of sound is being detected, a noise signal may also be detected. To solve this problem, the pulse signal is repeated several times (such as three or five) per second and the detection steps are repeated at the same frequency to obtain consistent values. Since the noise impulses are irregular, a desired signal can be differentiated from noise impulses after a number of repetitions. Although this requires the pulse to be of the same wave form during each repetition, typical electronic pulsers provide such repetitive pulses of constant wave form.

In this regard, it should be noted that apparatus other than the pulse generator 30 and electronic ultrasonic transducer 2 may be used, in accordance with the present invention, to generate the pulses. For example a mechanical sound generating device, such as a simple hammer, which exerts mechanical blows and which may be arranged for providing blows with the necessary repetitions, may be used.

In accordance with the present invention, the transducers 2 and 4 may be piezoelectric devices, electromagnetic-acoustic devices (EMAT), magnetostrictive devices, or other devices capable of producing a sound wave or vibration in the wall of the enclosure. In addition, the detector may also be an accelerometer or other device which is capable of converting the vibrations into electrical signals.

Figure 3:
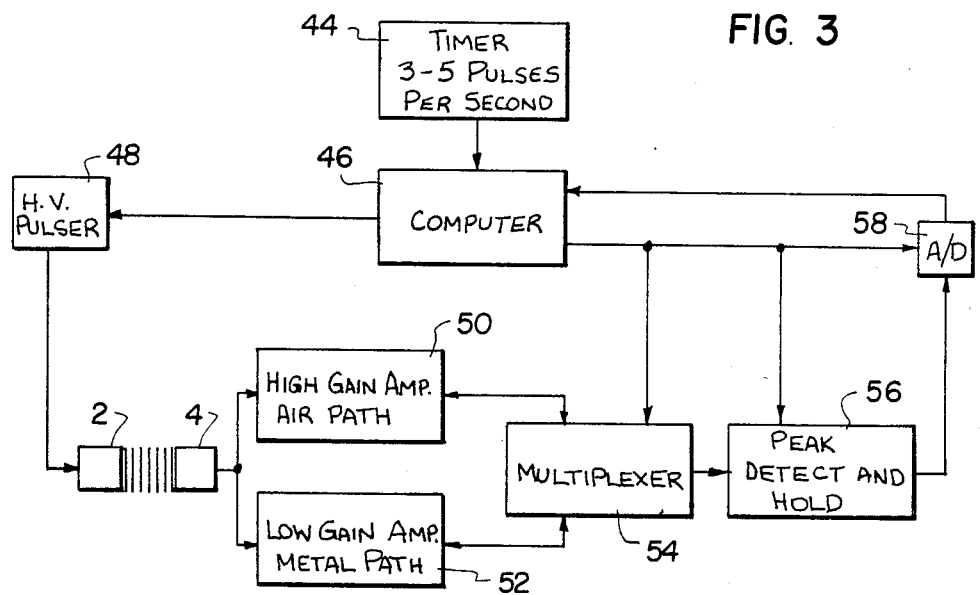
FIG. 3 is a block diagram showing an arrangement of test equipment embodying the invention.
Figure 4:
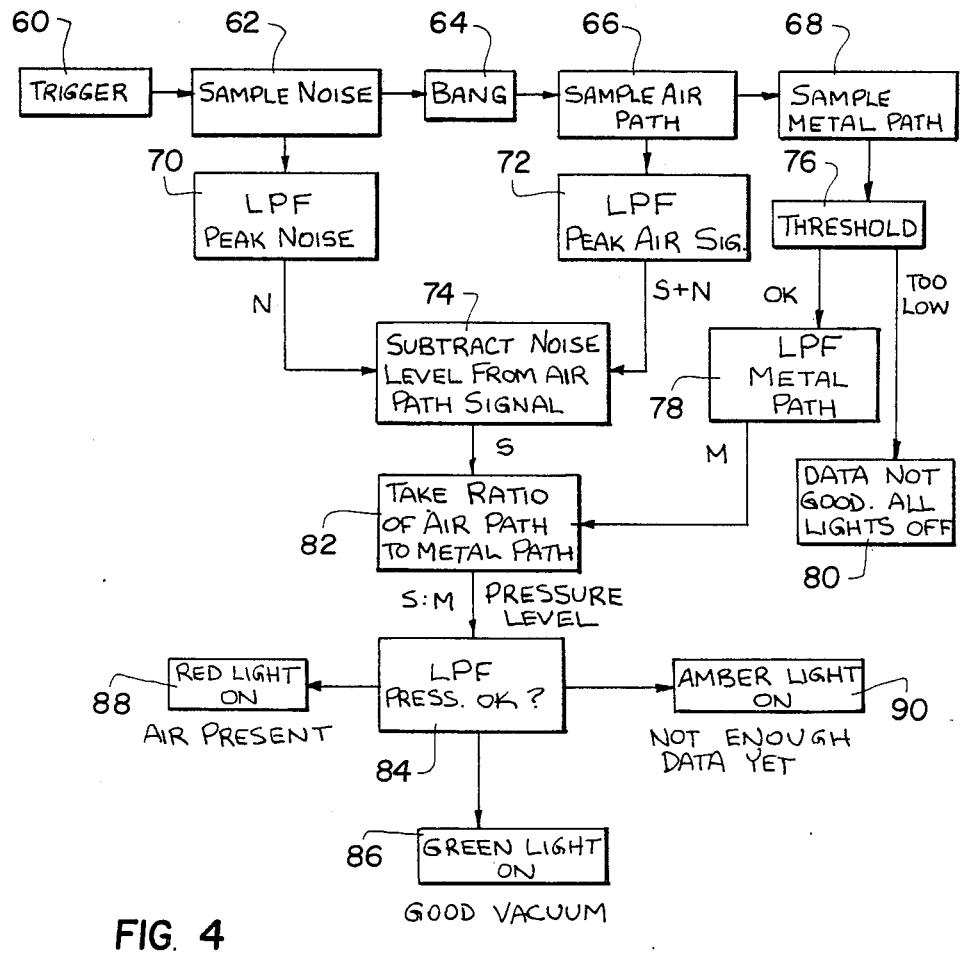
FIG. 4 is a flowchart showing the steps of a computer program for detecting the pressure condition in accordance with the invention.

FIGS. 3 and 4 illustrate a more complex device and computer program which is contemplated for practicing the invention. In FIG. 3, a timer 44 is provided for generating pulses at a rate preferably of from about 3 to 5 pulses per second. A faster pulse rate may cause distorted results since the tubes 14 and 16 may still be ringing from a previous sonic wave when a subsequent pulse is generated. Timer 44 is connected to a computer 46 which drives a sonic pulser 48 connected to transducer 2.

Transducer 4 is connected to a high gain amplifier 50 and a low gain amplifier 52 which are both connected to and controlled by computer 46 over a multiplexer. Since the portion of the sonic wave moving through the space will certainly be much weaker than the portion of the sonic wave moving through the metal path, the high gain amplifier is selected by multiplexer 54 during the period when the sound from the air path is expected and the low gain amplifier 52 is selected by multiplexer 54 during the period when the sound from the metal path is expected.

A peak detector and hold circuit 56 is connected to the output of multiplexer 54 for detecting and holding the highest voltage value during the respective air and metal path detection cycles. The output of this circuit is applied to an analog to digital converter 58 which returns a signal proportional to the peak values to computer 46 which can then be provided with suitable indicating means. Circuitry for such a device is commonly known to those of ordinary skill in the art to which this invention pertains.

As noted above, FIG. 4 illustrates a computer program for processing and indicating the results of the detection method. Since, as a practical matter, the inventive method and apparatus is intended for use usually in the field such as at an oil drilling site it is desirable to avoid sophisticated indicating equipment and analytical requirements as much as possible. In the interests of presenting as simple a display as possible, a technique using three indicating lights is contemplated. A red light would indicate the presence of air in excess of the threshold amount in the annular space of the tubing. An amber light would indicate that testing is still in progress, and a green light would indicate that a pressure below the threshold pressure exists in the annular space and that therefore the insulated steam injection tube being examined is considered acceptable for use.

As illustrated in FIG. 4, a trigger signal 60 samples noise at 62 and causes a burst of sound at 64. With suitable timing equipment, the air or space path is sampled at 66 and, thereafter, the metal or enclosure material path is sampled at 68.

The noise signal from 62 is processed in a low pass filter 70 or noise detection means for detecting a noise signal at second point 5 to generate a noise signal designated N, which is supplied to a comparator 74.

The signal from the air path sampling is processed in a low pass filter 72 or first sonic wave detection means for detecting a sonic wave portion passing through the space and generates a signal corresponding to the peak air path signal plus noise signal designated S+N.

The noise signal is then subtracted from the composite noise plus air path signal in subtractor or comparator 74 connected to low pass filter 70 and generates a corrected first sonic wave portion signal designated S corresponding to the sound received from the air pathway. If S=0, there is no sound passing through the space and it can be assumed that a sufficient vacuum has been maintained within the enclosure.

Meanwhile, the metal path signal is processed in a threshold unit 76 connected to low pass filter 78 which compares the signal from 68 with a minimum threshold allowed signal. If the signal from 68 is too low, which means there is improper acoustic coupling or some other problem in the equipment, a unit 80 switches all lights off indicating that the measurements are inadequate and cannot be used for correct processing.

If the metal path signal is high enough above the threshold value as determined by the threshold unit 76, it is processed in a further low pass filter 78 or second sonic wave detection means for detecting a sonic wave portion passing through the enclosure material and the peak metal signal is compared with the peak air signal in a ratio unit 82. This takes the ratio of the amplitudes between corrected first air path signal S and the second sonic metal path M which is processed in another low pass filter 84. If the ratio is low enough, a green light at 86 is lit indicating the vacuum is good. If the ratio is not low enough, a red light at 88 is lit indicating excessive air is present in the system. An amber light at 80 remains lit during the processing. It is noted that a number of samples, preferably at least 3 samples, must be taken which are consistent with each other before the red or green lights 88 or 86 will light indicating a completed result on the display means connected to ratio unit 82.

The low pass filters are provided to smooth and average the data. The filtering program is also provided to reject any obvious bad data based on data reject criteria which it is believed can be preset in the filtering program.

While specific embodiments of the invention have been shown and described in detail to illustrate the application of the principles of the invention, it will be understood that the invention may be embodied otherwise without departing from such principles.

What is claimed is:

1. A method of detecting the presence of a gaseous substance within the space bounded by an enclosure comprising:

providing a sonic wave at a first point on the inner wall of said enclosure whereby at least a first portion of said sonic wave travels in the material of the enclosure and a second portion of said sonic wave may travel through a gaseous substance in the space;

selecting a second point on the outer wall of said enclosure which second point is separated from said first point by the space;

determining whether a second portion of said sonic wave traveling through a gaseous substance in the space arrives at said second point;

determining the length of time it takes for a sonic wave to travel through a gaseous substance in the space from said first point to said second point;

providing a path length for travel of said first portion of said sonic wave through the material such that the first portion will arrive at said second point at a later time than the time in which a second portion of said sonic wave which may travel through a gaseous substance in the space will arrive at said second point; and determining whether a portion of said sonic wave arrives at said second point at said time in which a second portion of said sonic wave which may travel through a gaseous substance in the space is calculated to arrive at said second point.

2. A method according to claim 1, including comparing the amplitudes of detected portions of said sonic wave and determining if any of said detected portions has an amplitude corresponding to the amplitude of a sonic wave portion which travels through a gaseous substance in the space.

3. A method according to claim 1, including identifying the sonic wave portions which arrive at said second point by the length of time between generation and detection thereof.

4. A method according to claim 3, including comparing the amplitudes of detected portions of said sonic wave and determining if any of said detected portions has an amplitude corresponding to the amplitude of a sonic wave portion which travels through a gaseous substance in the space.

5. A method according to claim 3 including detecting sonic noise, substracting the sonic noise from an initially detected second portion of the sonic wave to obtain a corrected second portion of a sonic wave and thereafter taking the ratio between the corrected second portion of the sonic wave and the first portion of the sonic wave.

6. A method according to claim 5 including comparing the detected first portion of the sonic wave with a threshold value therefore and, only if the detected first portion of the sonic wave is above the threshold value, taking the ratio between the second portion and the first portion of the sonic wave.

7. A method according to claim 6, including repeating said initial detecting of the second portion of the sonic wave and said detecting of the first portion of the sonic wave a plurality of times and obtaining a consistent value for the first and second portions of the sonic wave.

8. A method according to claim 1, wherein the enclosure comprises an inner tube, an outer tube around said inner tube and defining an annular space therewith, and an end connection between said inner and outer tubes closing said annular space, said first and second points being spaced from said connection.

9. A method according to claim 8, including determining the length of time it takes for a sonic wave to travel through a gaseous substance in the space from said first point to said second point; and determining whether a portion of said sonic wave arrives at said second point at said time at which a second portion of said sonic wave which may travel through a gaseous substance in the space is calculated to arrive at said second point.

10. A method according to claim 8, including comparing the amplitudes of detected portions of said sonic wave and determining if any of said detected portions has an amplitude corresponding to the amplitude of a sonic wave portion which travels through a gaseous substance in the space.

11. A method according to claim 8, including identifying the sonic wave portions which arrive at said second point by the length of time between generation and detection thereof.

12. A method according to claim 11, including comparing the amplitudes of detected portions of said sonic wave and determining if any of said detected portions has an amplitude corresponding to the amplitude of a sonic wave portion which travels through a gaseous substance in the space.

13. A method of detecting the presence of a gaseous substance within the space bounded by an enclosure comprising:
   providing a sonic wave at a first point on the inner wall of said enclosure;
   selecting a second point at a position on the outer wall of said enclosure relative to the first point such that the length of time it takes a portion of the sonic wave to travel from the first to the second point through a gaseous substance in the space is less than the length of time it takes a portion of the sonic wave to travel from the first to the second point through the material comprising the enclosure without passing through the space;
   detecting the sonic wave at the second point; and
   comparing the period of time between the generation and initial detection of the sonic wave to the period of time it takes a sonic wave portion to travel from the first to the second point through a gaseous substance in the space.

14. A device for detecting the presence of a gaseous substance in a space bounded by an enclosure, comprising:
   sonic wave generating means including a first sonic transducer for generating a sonic wave;
   sonic wave detection means including a second transducer for detecting a sonic wave comprising a high gain amplifier and a low gain amplifier both connected to said second transducer and multiplexer means for switching to said high gain amplifier for detection of a portion of a sonic wave passing through a gaseous substance in the space and for switching to said low gain amplifier for detecting a portion of a sonic wave passing through the enclosure material without passing through the space; and
   mounting means connected to said first and second transducers for holding said first transducer at a first point on the inner wall of said enclosure and for holding said second transducer at a second point on the outer wall of said enclosure separated from said first point by the space such that a sonic wave portion passing through a gaseous substance in the space will reach said second transducer before a sonic wave portion passing along a path through the material comprising the enclosure.

15. A device according to claim 14, wherein said sonic wave generating means comprises an electronic pulser and piezoelectric transducer for generating a plurality of short ultrasonic wave pulses.

16. A device according to claim 14, wherein said mounting means comprise a first arm connected to said first transducer and a second arm connected to said second transducer, hinge means connected between said first and second arms for hinging said first and second arms together, and biasing means for biasing said first and second arms in a direction to urge said first and second transducers together, a length of said first and second arms being selected to permit positioning of said first transducer at the first point and said second transducer at the second point.

17. A device for detecting the presence of a gaseous substance in a space bounded by an enclosure, comprising:
   sonic wave generating means including a first sonic transducer for generating a sonic wave;
   sonic wave detecting means including a second sonic transducer for detecting a sonic wave including noise detection means for detecting a noise signal at the second point, first sonic wave detection means for detecting a sonic wave portion passing through the space and second sonic wave detection means for detecting a sonic wave portion passing through the enclosure material, a subtractor connected to said noise detection means for subtracting a noise signal from a first sonic wave portion detected by said first sonic wave means to generate a corrected first sonic wave portion signal, ratio means connected to said subtractor and to said second sonic wave portion detection means for taking a ratio of the amplitudes between the corrected first sonic wave portion signal and the second sonic wave portion signal, and display means connected to said ratio means for indicating the presence or absence of a gaseous substance above a threshold amount in the space depending on the magnitude of a ratio from said ratio means; and
   mounting means connected to said first and second transducers for holding said first transducer at a first point on the inner wall of said enclosure and for holding said second transducer at a second point on the outer wall of said enclosure separated from said first point by the space such that a sonic wave portion passing through a gaseous substance in the space will reach said second transducer before a sonic wave portion passing along a path through the material comprising the enclosure.

18. A device according to claim 17, including threshold means connected to said second sonic wave portion detection means for comparing a second sonic wave portion passing through the enclosure material with a threshold value therefor, and passing the second sonic wave signal to the ratio means only if the second sonic wave signal is above the threshold value.

19. A device according to claim 17, wherein said mounting means comprises a first arm connected to said first transducer and a second arm connected to said second transducer, hinge means connected between said first and second arms for hinging said first and second arms together, and biasing means for biasing said first and second arms in a direction to urge said first and second transducers together, a length of said first and second arms being selected to permit positioning of said first transducer at the first point and said second transducer at the second point.

* * * * *